US010974032B2

(12) United States Patent
Noar

(10) Patent No.: US 10,974,032 B2
(45) Date of Patent: Apr. 13, 2021

(54) BALLOON STRUCTURE WITH ANCHORING PORTIONS FOR ANCHORING IN A BODILY PASSAGE

(71) Applicant: Mark D. Noar, Owings Mills, MD (US)

(72) Inventor: Mark D. Noar, Owings Mills, MD (US)

( * ) Notice: Subject to any disclaimer, the term of this patent is extended or adjusted under 35 U.S.C. 154(b) by 285 days.

(21) Appl. No.: 15/623,506

(22) Filed: Jun. 15, 2017

(65) Prior Publication Data

US 2018/0104457 A1 Apr. 19, 2018

Related U.S. Application Data

(60) Provisional application No. 62/408,292, filed on Oct. 14, 2016.

(51) Int. Cl.
*A61M 25/10* (2013.01)
*A61B 90/00* (2016.01)
(Continued)

(52) U.S. Cl.
CPC ..... *A61M 25/1011* (2013.01); *A61B 1/00082* (2013.01); *A61B 18/00* (2013.01);
(Continued)

(58) Field of Classification Search
CPC .............. A61M 25/1011; A61M 29/02; A61M 25/0125; A61M 25/04; A61M 2025/105;
(Continued)

(56) References Cited

U.S. PATENT DOCUMENTS 5,460,610 A * 10/1995 Don Michael .... A61M 25/0133
604/101.03
6,488,653 B1 12/2002 Lombardo
(Continued)

FOREIGN PATENT DOCUMENTS

WO 2015153595 A1 10/2015

OTHER PUBLICATIONS

International Search Report & Written Opinion in PCT/US2017/036943 dated Aug. 22, 2017.
(Continued)

*Primary Examiner* — Jenna Zhang
(74) *Attorney, Agent, or Firm* — Manelli Selter PLLC; Edward Stemberger

(57) ABSTRACT

A balloon structure includes a proximal balloon portion having a first internal volume, a distal balloon portion having a second internal volume, and a central balloon portion disposed between and joined with the proximal and distal balloon portions. The central balloon portion has a third internal volume isolated from the first and second internal volumes. A first lumen is associated with the third internal volume to direct pressure to the third internal volume for inflation of the central balloon portion. At least one second lumen is associated with the first and second internal volumes to direct pressure to the first and second internal volumes for inflation of the proximal balloon portion and the distal balloon portion. Whereby, upon inflation, the central balloon portion dilates, or delivers other treatments to tissue in the passage, with the proximal and distal balloon portions limiting movement of the balloon structure in the passage.

9 Claims, 2 Drawing Sheets

(51) Int. Cl.
*A61M 29/02* (2006.01)
*A61B 18/00* (2006.01)
*A61B 18/14* (2006.01)
*A61B 18/04* (2006.01)
*A61B 1/00* (2006.01)
*A61M 25/01* (2006.01)
*A61M 25/04* (2006.01)

(52) U.S. Cl.
CPC .......... *A61B 18/04* (2013.01); *A61B 18/1492* (2013.01); *A61B 90/361* (2016.02); *A61B 90/37* (2016.02); *A61M 25/0125* (2013.01); *A61M 29/02* (2013.01); *A61B 2018/00285* (2013.01); *A61B 2018/00345* (2013.01); *A61B 2018/00482* (2013.01); *A61B 2018/00505* (2013.01); *A61B 2018/00577* (2013.01); *A61B 2018/00982* (2013.01); *A61B 2090/3782* (2016.02); *A61M 25/04* (2013.01); *A61M 2025/105* (2013.01); *A61M 2025/1015* (2013.01)

(58) Field of Classification Search
CPC ....... A61M 2025/1015; A61B 1/00082; A61B 90/361; A61B 18/1492; A61B 18/04; A61B 90/37; A61B 18/00; A61B 2090/3782; A61B 2018/00982; A61B 2018/00577; A61B 2018/00505; A61B 2018/00482; A61B 2018/00345; A61B 2018/00285
See application file for complete search history.

(56) References Cited

U.S. PATENT DOCUMENTS

| | | | |
|---|---|---|---|
| 6,527,692 | B1 | 3/2003 | Weinberger |
| 7,655,005 | B2 | 2/2010 | Bhola |
| 8,528,563 | B2 | 9/2013 | Gruber |
| 8,597,239 | B2 | 12/2013 | Gerrans et al. |
| 8,790,299 | B2 | 7/2014 | Gunday |
| 9,339,442 | B2 | 5/2016 | Tai et al. |
| 2004/0059290 | A1 | 3/2004 | Palasis |
| 2006/0095066 | A1 | 5/2006 | Chang et al. |
| 2007/0288051 | A1 | 12/2007 | Beyer et al. |
| 2010/0121270 | A1* | 5/2010 | Gunday ................ A61M 1/008 604/98.01 |
| 2012/0078029 | A1 | 3/2012 | Subramanian |
| 2012/0226230 | A1* | 9/2012 | Gerrans ............. A61M 25/1011 604/103.01 |
| 2012/0259216 | A1* | 10/2012 | Gerrans ......... A61B 17/320725 600/435 |
| 2013/0030410 | A1 | 1/2013 | Drasler et al. |
| 2013/0116549 | A1* | 5/2013 | Gunday .................. A61B 1/32 600/424 |
| 2015/0290438 | A1 | 10/2015 | Gerrans et al. |
| 2016/0310200 | A1* | 10/2016 | Wang .................... A61B 18/04 |

OTHER PUBLICATIONS

Supplementary European Search Report in EP17860422 dated Jul. 10, 2020.
Supplementary Partial European Search Report & Provisional Opinion in EP 17860422 dated Feb. 20, 2020.

* cited by examiner

BALLOON STRUCTURE WITH ANCHORING PORTIONS FOR ANCHORING IN A BODILY PASSAGE

FIELD

The embodiment relates to a balloon structure for use in a human body and, more particularly, to an endoscopic balloon structure having anchoring portions at opposing ends thereof to anchor the balloon in a passage of the body a while a central portion of the balloon structure performs dilation or additional therapeutic treatment in the passage.

BACKGROUND

Current endoscopic dilation balloons come in various sizes and are generally only of cylindrical shape. The conventional balloons are made of various materials and sizes can be either one specific size or balloons can be of a range of sizes (10-12-14 mm) depending on the pressure in the balloon. Balloons are either TTS (through the endoscope) or wire guided (over a wire and outside the endoscope).

A problem with current dilation balloons is that they require the operator to hold the balloon in place. This can be difficult if the operator is dilating or positioning across a narrowed area like a sphincter or stenotic or strictured area. This difficulty is due to a few factors such as: 1) the peristalsis of the organ is constantly moving the device down the tract, displacing the balloon, or 2) the narrowed area makes it difficult to wedge in place and maintain position (balloon is annular, environment is slippery, pressure at the narrowed area exerts force to push balloon up or down.

Thus, there is a need to provide a balloon structure with anchoring portions to self-anchor the balloon structure during treatment.

SUMMARY

An objective of the embodiment is to fulfill the need referred to above. In accordance with the principles of an embodiment, this objective is achieved by providing a balloon structure for dilating or otherwise administering therapy to tissue in a bodily passage. The balloon structure includes a proximal balloon portion having a first internal volume, a distal balloon portion having a second internal volume, and a central dilation and/or positioning therapeutic balloon portion disposed between and joined with the proximal balloon portion and the distal balloon portion. The central dilation/therapeutic balloon portion has a third internal volume isolated from the first and second internal volumes. A first lumen is associated with the third internal volume to direct pressure to the third internal volume for inflation of the central balloon portion. At least one second lumen is associated with the first and second internal volumes to direct pressure to the first and second internal volumes for inflation of the proximal balloon portion and the distal balloon portion. Whereby, upon inflation of each of the proximal, distal and central balloon portions, the proximal balloon portion and the distal balloon portion are constructed and arranged to limit movement of the balloon structure in the passage while the central balloon portion is constructed arranged to dilate tissue in the passage, or maintain tissue apposition for the delivery of therapies or for obtaining images of the tissue.

In accordance with another aspect of an embodiment, a method anchors a balloon structure in a bodily passage. The balloon structure has a proximal balloon portion having a first internal volume, a distal balloon portion having a second internal volume, and a central balloon portion disposed between and joined with the proximal balloon portion and the distal balloon portion. The central balloon portion has a third internal volume isolated from the first and second internal volumes. The balloon structure is inserted into the bodily passage. The internal volumes of at least each of the proximal balloon portion and the distal balloon portion are inflated to thereby limit movement of the balloon structure in the bodily passage. Once anchored, the central balloon portion can be inflated to dilate tissue and/or energy or other therapeutic measures can be delivered to the tissue, and/or imaging of the tissue can be obtained.

Other objectives, features and characteristics of the present embodiment, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF THE EXEMPLARY EMBODIMENTS

Figure 1:
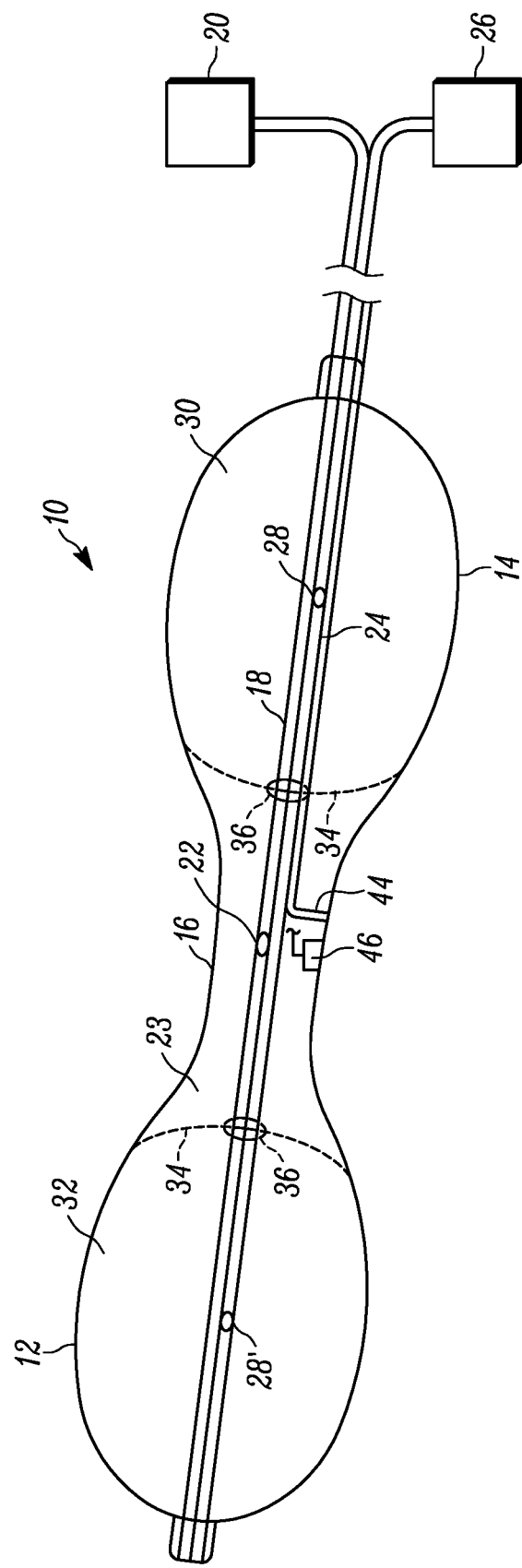
FIG. 1 is an enlarged view of a dilation balloon structure provided in accordance with a first embodiment, shown in an uninflated state.

With reference to FIG. 1, an enlarged view of a dilation balloon structure, generally indicated at 10, is shown in an uninflated state. The balloon structure 10 comprises a distal balloon portion 12, a proximal balloon portion 14, and a central dilation balloon portion 16 disposed between and joined with the distal balloon portion 12 and the proximal balloon portion 14.

The balloon structure 10 includes a first lumen 18 for connection with a first source of pressure 20. The first lumen 18 includes an exit orifice 22 located in the internal volume 23 of the central dilation balloon portion 16 for inflating the balloon portion 16 using the first source of pressure 20. The balloon structure 10 includes at least a second lumen 24 for connection with a second source of pressure 26. The second lumen 24 includes an exit orifice 28 located in the internal volume 30 of the balloon portion 14 and an exit orifice 28' located in the internal volume 32 of the balloon portion 12 for inflating the balloon portions 12 and 14 using the second source of pressure 26. A guide wire (not shown) could be provided to extend along with the lumens 18 and 24 if need in placing the balloon structure 10. Instead of using a single second lumen 24 to inflate the balloon portions 12 and 14 generally simultaneously, a separate lumen (not shown) could be used to inflate each balloon portion 12 and 14 individually. Although the pressure sources 20 and 26 are shown preferably to be separate items, it is contemplated that a single pressure source could provide pressure individually to each of the lumens 18 and 24.

The internal volumes 30 and 32 of the respective balloon portions 14 and 12, are isolated from the internal volume 23 of the central dilation balloon portion 16 by walls 34, and seal structure 36 associated with the walls 36 and the lumens 18 and 24, preventing air to pass around the lumens 18 and 24 and through the walls 36. Thus, the balloon portions 12 and 14 can be inflated independently of the balloon portion 16.

Figure 2:
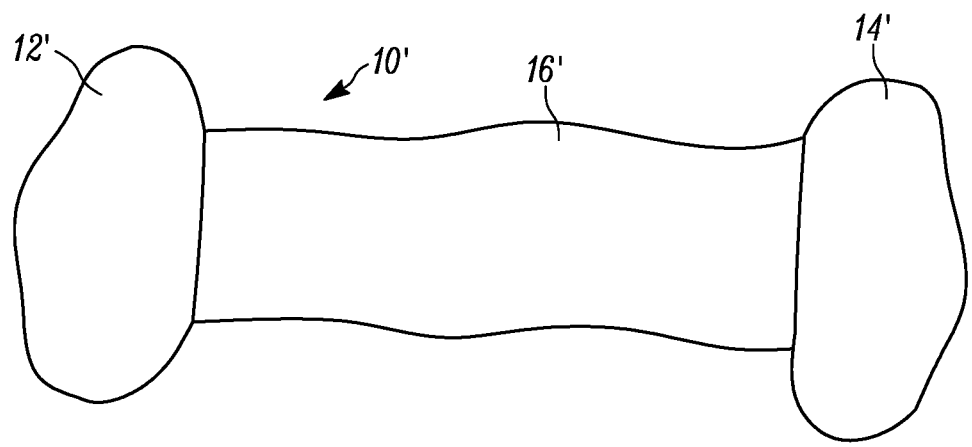
FIG. 2 is an enlarged view of a dilation balloon structure provided in accordance with a second embodiment, shown in an uninflated state and without the lumens thereof.

In the embodiment of FIG. 1, the balloon portions 12, 14 and 16 are manufactured integrally by employing the separation walls 34 as noted above. Alternatively, as shown in FIG. 2, the balloon portions 12', 14' and 16' can be manufactured as three separate balloons that are then joined together to comprise the balloon structure 10'. As with the embodiment of FIG. 1, lumens (not shown in FIG. 2) with appropriate sealing would be provided to inflate balloon portions 12' and 14' independently of inflation of the balloon portion 16'.

The central dilation balloon portion 16 is preferably made of a material having sufficient hoop strength so as to dilate the desired tissue. Balloon portions 12 and 14 are preferably made of the same material, which can be the same material that portion 16 is made from. However, since balloon portions 12 and 14 do not perform a dilation function, balloon portions 12 and 14 can be made of a material that is different from that of balloon portion 16 since the function of balloon portions 12 and 14 is merely to anchor the balloon structure 10, as will be explained below. For example, the balloon portions 12 and 14 can be made, for example, from latex while balloon portion 16 can be made, for example, from polyethylene terephthalate (PET), irradiated polyethylene, or nylon.

Figure 3:
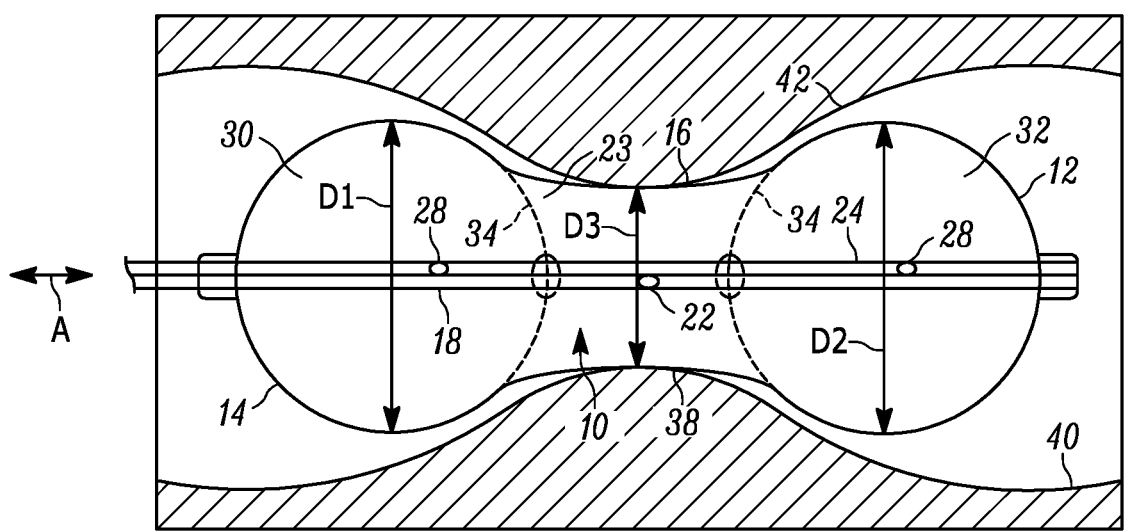
FIG. 3 is a view of the dilation balloon structure of FIG. 1 shown in an inflated state dilating a restriction in a bodily passage, with anchoring portions anchoring the balloon structure in the passage.

With reference to FIGS. 1 and 3, the balloon structure 10 can be guided (e.g., endoscopically by wire) into a generally tubular bodily passage 40 that has a tissue restriction 38. Once the central dilation balloon portion 16 is in place adjacent to the restriction 38, the proximal and distal balloon portions 12 and 14 can be inflated via source 26 to increase the respective internal volumes 32, 30 thereof. Thereafter, the central dilation balloon portion 16 is independently inflated via source 20 to dilate the tissue restriction 38 in the passage 40. Advantageously, the proximal and distal balloon portions 12 and 14 are disposed in the passage 40 on opposing ends of the restriction 38 and are constructed and arranged to self-anchor the balloon structure 10 within the passage 40. Thus, the balloon portions 12 and 14 can be considered to be anchor portions of the balloon structure 10, preventing slippage or migration during dilation. To facilitate such anchoring, it can be seen that the inflated diameters D1 and D2 of the balloon portions 12 and 14 are larger than the inflated diameter D3 of the central dilating balloon portion 16. For example, when D3 is 20 mm, D1 and D2 can be about 22-24 mm. Thus, the balloon portions 12 and 14 limit movement of the balloon structure 10 along the axis A. Furthermore, depending on the passage dimensions and the inflation size of the balloon portions 12 and 14, the balloon portions 12 and 14 could be inflated to engage the inner surface 42 of the passage 40 for further anchoring.

The size of the balloon portions 12, 14 and 16 upon inflation can be selected for the desired application. Furthermore, the distance between the proximal and distal balloon portions 12 and 14 can also be selected based on the desired applications. Applications for the balloon structure 10 include use, for example, in the gastrointestinal tract, urinary tract, vascular tract, or any other bodily passage that permits insertion of the balloon structure 10.

The balloon structure 10 can be used for purposes other than just for dilating tissue due to the anchoring features thereof. The balloon structure 10 can have, integral therewith or separate therefrom, energy delivery structure 44 (FIG. 1) to deliver a energy to tissue near the bodily passage 40. Such energy can include (but is not limited to) radio frequency energy, radiation energy, infrared energy, heat energy, electrical energy, and ablation energy. Delivering energy to tissue and/or ablating tissue is made easier since the balloon structure 10 is anchored in the bodily passage 40 as noted above. In the embodiment, the energy delivery structure 44 is preferably disposed in the internal volume 23 of the central dilation balloon portion 16. For example, if radiation energy is employed, the energy delivery structure 44 can be in the form of a lumen extending to the central balloon portion 16 to deliver the energy through the balloon structure 10 to tissue surrounding the central dilation balloon portion 16. It is contemplated that the energy delivery structure 44 could be manipulated to extend through the balloon portion 14 to the central dilation balloon portion 16 and to extend through a wall of the central dilation balloon portion 16 to engage (e.g., ablate) tissue while anchored, while ensuring appropriate sealing of the internal volume 23. Instead of ablating or destroying tissue, the energy delivery structure 44 can deliver energy to stimulate muscle growth of tissue near the bodily passage 40. The energy delivery structure 44 can also be used to mark tissue for later treatment, for example, by delivering heat to gently burn portions of the tissue so as to mark the tissue.

The central balloon portion 16 can include imaging structure 46 fixed therein. For example, at least the central dilation balloon portion 16 can be transparent and the imaging structure 46 can be disposed in the internal volume 23 thereof to obtain images of tissue near the bodily passage 40. For example, the imaging structure can comprise an image sensor such as a CCD (charge-coupled device) or a CMOS (complementary metal-oxide semiconductor) or can comprise a camera to capture images of the tissue adjacent to the central balloon portion 16 while the anchored. Alternatively, the imaging structure 46 can use ultrasound imaging.

Delivering energy and/or capturing an image of tissue as mentioned above is preferably performed while all three balloon portions 12, 14 and 16 are inflated. The inflated central balloon portion 16 maintains tissue apposition for delivery of therapy (e.g., energy) to the tissue or while images of the tissue are obtained, while balloon portions 12 and 14 provide the anchoring function. However, these functions can be performed only when balloon portions 12 and 14 are inflated and thus anchored in the bodily passage 40.

Thus, it can be seen that the balloon structure 10 provides an effective means of self-anchoring in bodily tissue during dilation, energy treatment or imaging of the tissue.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A balloon structure for providing therapy to tissue in a bodily passage comprising:
   a proximal balloon portion having a first internal volume,
   a distal balloon portion having a second internal volume, a central balloon portion joined between and adjacent to each of the proximal balloon portion and the distal balloon portion, the central balloon portion having a third internal volume isolated from the first and second internal volumes, a first lumen associated with the third internal volume to direct pressure to the third internal volume for inflation of the central balloon portion, and at least one second lumen associated with the first and second internal volumes to direct pressure to the first and second internal volumes for inflation of the proximal balloon portion and the distal balloon portion, and whereby, upon inflation of each of the proximal, distal and central balloon portions, the proximal balloon portion and the distal balloon portion are constructed and arranged to limit movement of the balloon structure in the passage while the central balloon portion is constructed arranged to dilate tissue in the passage, or maintain tissue apposition for delivery of therapy to the tissue or for obtaining images of the tissue, wherein the balloon structure further comprises energy delivery structure in the form of a third lumen extending through the proximal balloon portion and having an end disposed in the third internal volume of the central balloon portion, the third lumen being a structure separate from the central and proximal balloon portions and constructed and arranged to deliver energy to stimulate growth of the tissue instead of destroying the tissue receiving the energy, while the central balloon portion is inflated and is in apposition to the tissue and while the proximal and distal balloon portions limit movement of the balloon structure in the passage, and wherein at least a portion of the energy delivery structure is disposed in the third internal volume so that the energy is delivered through the central balloon portion.

2. The balloon structure of claim 1, wherein the proximal balloon portion and the distal balloon portion are each constructed and arranged to have a diameter, in an inflated state, which is greater than a diameter, in an inflated state, of the central balloon portion.

3. The balloon structure of claim 1, wherein the proximal balloon portion and the distal balloon portion are each made from one material, while the central balloon portion is made from a material different from said one material.

4. The balloon structure of claim 1, wherein the energy delivery structure is constructed and arranged to deliver radio frequency energy, radiation energy, infrared energy, heat energy, or electrical energy.

5. The balloon structure of claim 1,
wherein at least the central balloon portion is transparent and the balloon structure further comprises imaging structure positioned adjacent to an internal wall of the balloon structure and fixed within the third internal volume and constructed and arranged to obtain an image of the tissue near the bodily passage.

6. The balloon structure of claim 5, wherein the imaging structure comprises an image sensor or a camera.

7. The balloon structure of claim 6, wherein the image sensor comprises a CCD (charge-coupled device) or a CMOS (complementary metal-oxide semiconductor).

8. The balloon structure of claim 1, further comprises imaging structure constructed and arranged to obtain an ultrasound image of the tissue near the bodily passage.

9. A balloon structure for providing therapy to tissue in a bodily passage comprising:

a proximal balloon portion having a first internal volume, a distal balloon portion having a second internal volume, a central balloon portion joined between and adjacent to each of the proximal balloon portion and the distal balloon portion, the central balloon portion having a third internal volume isolated from the first and second internal volumes, a first lumen associated with the third internal volume to direct pressure to the third internal volume for inflation of the central balloon portion, and at least one second lumen associated with the first and second internal volumes to direct pressure to the first and second internal volumes for inflation of the proximal balloon portion and the distal balloon portion, and whereby, upon inflation of each of the proximal, distal and central balloon portions, the proximal balloon portion and the distal balloon portion are constructed and arranged to limit movement of the balloon structure in the passage while the central balloon portion is constructed arranged to dilate tissue in the passage, or maintain tissue apposition for delivery of therapy to the tissue or for obtaining images of the tissue, wherein the balloon structure further comprises energy delivery structure in the form of a third lumen extending through the proximal balloon portion and having an end disposed in the internal volume of the central balloon portion, the third lumen being a structure separate from the central and proximal balloon portions and constructed and arranged to deliver energy as the therapy to the tissue, while the central balloon portion is inflated and is in apposition to the tissue and while the proximal and distal balloon portions limit movement of the balloon structure in the passage, and wherein at least the end of the third lumen is constructed and arranged to be manipulated to extend outward through an outer wall of the central balloon portion to engage tissue, while ensuring sealing of the internal volume of the central balloon portion.

* * * * *